United States Patent [19]

Müller et al.

[11] 4,007,183
[45] Feb. 8, 1977

[54] STABILISERS FOR POLYOLEFINES

[75] Inventors: Helmut Müller, Binningen; Siegfried Rosenberger, Riehen, both of Germany; Kurt Schwarzenbach, Basel, Switzerland

[73] Assignee: Ciba-Geigy Corporation, Ardsley, N.Y.

[22] Filed: May 20, 1974

[21] Appl. No.: 471,408

Related U.S. Application Data

[62] Division of Ser. No. 150,757, June 7, 1971, Pat. No. 3,850,918.

[30] Foreign Application Priority Data

June 17, 1970 Sweden .......................... 9182/70
Oct. 2, 1970 Sweden .......................... 14666/70

[52] U.S. Cl. ............................................. 260/249.8
[51] Int. Cl.$^2$ ........................................ C07D 251/48
[58] Field of Search ................................ 260/249.8

[56] References Cited

UNITED STATES PATENTS

| | | | |
|---|---|---|---|
| 3,367,899 | 2/1968 | Thoma et al. | 260/249.8 |
| 3,679,678 | 7/1972 | Koenig et al. | 260/249.8 |
| 3,920,611 | 11/1975 | del Rio et al. | 260/249.8 |
| 3,946,011 | 3/1976 | Gordon et al. | 260/249.8 |
| 3,957,726 | 5/1976 | Gordon | 260/249.8 |

*Primary Examiner*—Paul J. Killos
*Attorney, Agent, or Firm*—Nestor W. Shust

[57] ABSTRACT

New 4,6-disalicyloyl-hydrazino-s-triazines are stabilizers for polyolefines. They are prepared by reacting 4,6-dihydrazino-s-triazines with salicylol chloride.

5 Claims, No Drawings

STABILISERS FOR POLYOLEFINES

This is a Division of application Ser. No. 150,757, filed on June 7, 1971 now U.S. Pat. 3,850,918, issued Nov. 26, 1974.

DETAILED DESCRIPTION

The subject of the present invention are new compounds and their use for stabilising polyolefines.

Because of their physical and electrical properties, polyolefines, especially polypropylene, are very suitable for use as an insulating material in the electrical industry, especially for sleeving and coating copper wires, cables and other electrically conducting materials made of copper. Unfortunately, however, the said good properties of the polyolefines are worsened through the fact that in contact with transition metals, especially with copper, the polyolefines suffer an oxidative degradation catalysed by these metals. Additions of copper of less than 1%, for example, already cause an approximately hundred-fold lowering of the stability to oxidation of polypropylene.

In the patent literature, numerous types of compounds have already been described as additives for polyolefines for the purpose of stabilisation in the presence of copper; examples are hydroxybenzoic acid hydrazides or their substitution products. Thus it is known from British Patent Specification No. 1,093,383 to employ hydroxy-substituted benzoylhydrazides, such as salicylic acid hydrazide. Japanese Patent Specification No. 18,607/68 describes acylated salicylic acid hydrazides, especially N-acetyl-salicylic acid hydrazide, as additives. Whilst both these types of compounds show a certain effect, polypropylene stabilised therewith is still degraded significantly more rapidly in the presence of copper than is polypropylene which is not in contact with copper. Finally, U.S. Pat. No. 3,110,696 has disclosed the compound

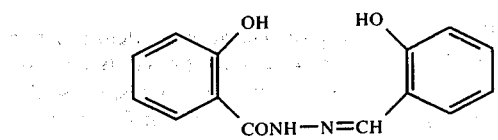

as a stabiliser against copper. Whilst this compound shows an excellent stabiliser action, it has the disadvantage of an inherent yellow colour, for which reason polyolefine stabilised therewith appears to have an undesirable yellow discolouration.

The same compound, and its nuclear-substituted derivatives, have been described as heat stabilisers for optionally crosslinked polyethylene filled with carbon black. These compounds, however, only show a limited action in polyethylene containing carbon black and are ineffective as heat stabilisers in the absence of carbon black.

It has now surprisingly been found that the new compounds of the formula I

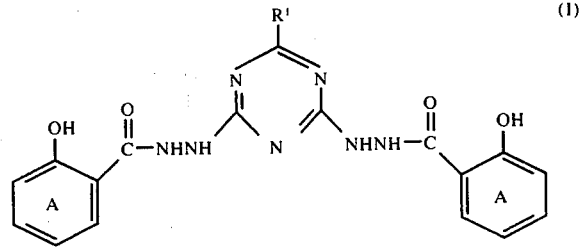

in which $R_1$ denotes hydrogen, alkyl with 1 to 18 carbon atoms, alkoxy with 1 to 18 carbon atoms, unsubstituted phenyl, phenyl substituted by lower alkyl groups, lower alkoxy groups, halogen and/or hydroxyl groups, the group

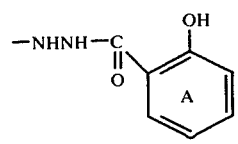

or the group

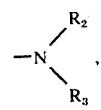

$R_2$ and $R_3$ independently of one another denote hydrogen, alkyl with 1 to 18 carbon atoms, cyclohexyl, benzyl, unsubstituted phenyl or phenyl substituted by 1 or 2 alkyl groups each having 1 to 8 carbon atoms, or $R_2$ and $R_3$ conjointly, with inclusion of the nitrogen atom, denote a saturated 5-membered to 7-membered heterocyclic ring, and the rings A are unsubstituted or are substituted by 1 to 2 alkyl groups each having 1 to 18 carbon atoms, an alkoxy group having 1 to 18 carbon atoms and/or 1 – 3 chlorine atoms, are very suitable for stabilising homopolymeric or copolymeric polyolefines especially against thermo-oxidative degradation, and that these compounds at the same time possess good colour properties.

The compounds of the formula I protect homopolymeric and copolymeric polyolefines especially against thermo-oxidative degradation in the presence of transition metals.

At the same time, the compounds according to the invention are not only excellent stabilisers, the action of which, both used along and in synergistic combinations with other stabilisers, in part distinctly surpasses the previously known classes of compounds described above, but also have the advantage of being colourless. This permits their incorporation into polyolefines without objectionably discolouring the latter. Additionally, all the abovementioned previously known compounds show the property of discolouring polyolefines under ageing conditions, whilst the compounds according to the invention remain largely colourless under these conditions, which represents a great technical advantage for long-term stabilisation.

In formula I, $R_1$ for example denotes an alkyl group of 1 to 18 carbon atoms, such as methyl, ethyl, propyl, butyl, pentyl, hexyl, octyl, decyl, dodecyl, tetradecyl, hexadecyl or octadecyl, an alkoxy group with 1 to 18 carbon atoms, such as methoxy, propoxy, butoxy, hexoxy, octoxy, decyloxy, dodecyloxy, hexadecyloxy or octadecyloxy, or a phenyl group which can be substituted by lower alkyl, such as methyl, ethyl, propyl or butyl, by lower alkoxy groups, such as methoxy, ethoxy, propoxy or butoxy, by halogen, such as chlorine or bromine, and by a hydroxyl group, the latter preferably being in the ortho-position. In the description and in the claims, lower alkyl or alkoxy groups denote alkyl or alkoxy groups with 1 to 4 carbon atoms. $R_1$ can be an unsubstituted, monosubstituted or disubstituted amino group, wherein the substituent or substituents can be unbranched or branched alkyl with 1 to 18 carbon atoms, for example methyl, ethyl, propyl, isopropyl, butyl, tert.-butyl, pentyl, hexyl, octyl, tert.-octyl, decyl, dodecyl, tetradecyl, hexadecyl or octadecyl. If $R_1$ is a phenyl substituted by 1 or 2 alkyl groups, the alkyl groups contain 1 to 8 carbon atoms and are, for example, methyl, ethyl, propyl, butyl, isobutyl, amyl, hexyl, octyl or isooctyl. $R_1$ can also be a five-membered to seven-membered heterocyclic group containing nitrogen in the nucleus, which is bonded via a nitrogen atom to the triazine ring of the compound of the formula I, for example the piperidine or the morpholine group. The nuclei A in the formula I can be substituted, for example by one or two identical or different alkyl groups of 1 to 18 carbon atoms, such as methyl, ethyl, propyl, isopropyl, butyl, tert.-butyl, pentyl, hexyl, octyl, tert.-octyl, decyl, dodecyl, tetradecyl, hexadecyl and octadecyl, or an alkoxy group with 1 to 18 carbon atoms, such as methoxy, propoxy, butoxy, hexoxy, decyloxy, dodecyloxy, hexadecyloxy or octadecyloxy.

Preferred metal deactivators amongst the compounds of the formula I are those in which $R_1$ denotes an alkyl group with 1 to 3 carbon atoms, an alkoxy group with 2 to 4, especially 3 and 4, carbon atoms, or the group

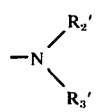

wherein $R_2'$ and $R_3'$ independently of one another are hydrogen, alkyl with 1 to 8 carbon atoms, cyclohexyl, benzyl or phenyl, or $R_2'$ and $R_3'$, with inclusion of the nitrogen atom, form the radical of pyrrolidine, piperidine, morpholine or hexamethyleneimine, and $R_2'$ and $R_3'$ together contain 1 to 8 carbon atoms, and $R_1$ and the substituents of A together contain at most 12 carbon atoms.

Compounds in which $R_2'$ and $R_3'$ independently of one another denote hydrogen, alkyl with 1 to 8 carbon atoms or phenyl, and $R_2'$ and $R_3'$ together contain 1 to 8 carbon atoms, are particularly preferred.

Preferred antioxidants amongst the compounds of the formula I are those in which $R_1$ denotes hydrogen, alkyl with 1 to 4 carbon atoms, alkoxy with 1 to 8 carbon atoms, unsubstituted phenyl, phenyl substituted by methyl groups, methoxy groups, halogen and/or hydroxyl groups, the group

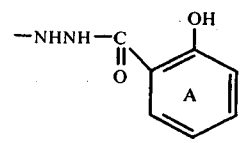

or the group

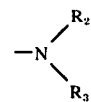

$R_2$ and $R_3$ independently of one another denote alkyl with 1 to 18 carbon atoms, cyclohexyl, benzyl, phenyl or phenyl substituted by 1 to 2 alkyl groups with 1 to 4 carbon atoms each, $R_2$ and $R_3$ together, with inclusion of the nitrogen atom, denote a saturated, 6-membered, heterocyclic ring and $R_3$ furthermore also denotes hydrogen, and the rings A are unsubstituted or are substituted by 1 to 2 alkyl groups with 1 to 12 carbon atoms each, an alkoxy group with 1 to 18 carbon atoms and/or chlorine, with $R_1$ and the substituents of A together containing at least 13 carbon atoms.

Particularly preferred compounds are those in which $R_1$ denotes alkyl with 1 or 2 carbon atoms, alkoxy with 1 to 4 carbon atoms, unsubstituted phenyl, phenyl substituted by 1 or 2 methyl groups, chlorine, methoxy or hydroxyl, the group

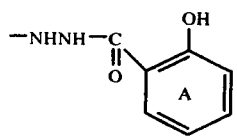

or the group

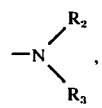

$R_2$ and $R_3$ independently of one another denote alkyl with 1 to 18 carbon atoms, cyclohexyl, benzyl or phenyl, or $R_2$ and $R_3$ together, with inclusion of the nitrogen atom, denote a piperidine or morpholine ring, and the rings A are unsubstituted or are substituted by 1 to 2 alkyl groups with 1 to 8 carbon atoms each, an alkoxy group with 1 to 18 carbon atoms and/or chlorine, with $R_1$ and the substituents of A together containing at least 13 carbon atoms.

Compounds of the formula I can be manufactured in the following ways:

a. Reaction of 1 mol of the compound of the formula II

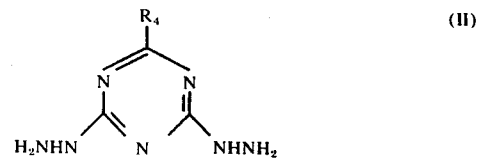

wherein $R_4$ denotes hydrogen, alkyl with 1 to 18 carbon atoms, alkoxy with 1 to 18 carbon atoms, unsubstituted phenyl, phenyl substituted by lower alkyl groups, lower alkoxy groups, halogen and/or hydroxyl groups, the group

wherein $R_2$ and $R_3$ have the meaning given under formula I, or the group

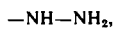

with 2, and in the case of $R_4 = -NHNH_2$, 3 mols of a compound of the formula III

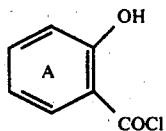

wherein the nucleus A can be substituted as indicated under formula I.

b. Reaction of 1 mol of the compound of the formula IV

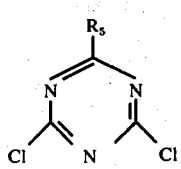

wherein $R_5$ denotes hydrogen, alkyl with 1 to 18 carbon atoms, alkoxy with 1 to 18 carbon atoms, unsubstituted phenyl, phenyl substituted by lower alkyl groups, lower alkoxy groups, halogen and/or hydroxyl groups, or the group

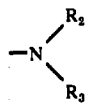

wherein $R_2$ and $R_3$ have the meaning indicated under formula I, with 2 mols of a compound of the formula V

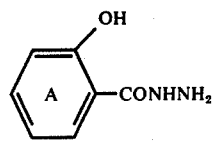

wherein A can be substituted as indicated under formula I.

c. Reaction of 1 mol of a compound of the formula VI

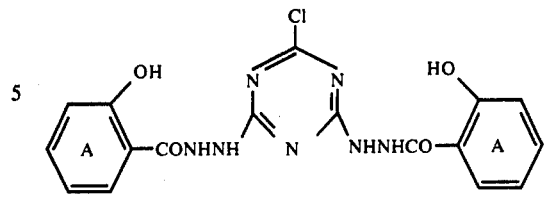

wherein the nuclei A can be substituted as indicated under formula I, with 1 mol of an amine of the formula VII

wherein $R_2$ and $R_3$ have the meaning indicated under formula I.

d. Reaction of 1 mol of cyanuric chloride with 3 mols of a compound of the formula V.

The compounds of the formula II are manufactured from 1 mol of the compounds of the formula IV and 2 mols of hydrazine, and in this case $R_5$ in the formula IV has the meaning of $R_4$ in the formula II.

The compounds of the formula VI are obtained from 1 mol of cyanuric chloride and 2 mols of the compound of the formula V.

The compounds according to the invention provide protection against thermo-oxidative degradation for polyolefines, preferably α-olefine polymers, such as polypropylene, optionally crosslinked polyethylene, polyisobutylene, polymethylbutene, polymethylpentene-1, polybutene-1, polyisoprene or polybutadiene; copolymers of the monomers on which the said homopolymers are based, such as ethylene-propylene copolymers, propylene-butene-1 copolymers, propylene-isobutylene copolymers, styrene-butadiene copolymers, ethylene-vinyl acetate copolymers, and terpolymers of ethylene and propylene with a diene, for example hexadiene, dicylcopentadiene or ethylidenenorbornene; and mixtures of the abovementioned homopolymers, for example mixtures of polypropylene and polyethylene, polypropylene and polybutene-1 or polypropylene and polyisobutylene. Polypropylene, and its mixtures and the copolymers which contain propylene units, are here preferred.

The new compounds are incorporated into the substrates at a concentration of 0.01 to 5.0% by weight, calculated relative to the material to be stabilised.

Preferably, 0.05 to 1.5, and particularly preferentially 0.1 to 0.8%, by weight of the new compounds, calculated relative to the material to be stabilised, are incorporated into the substrates.

The incorporation can take place before, during or preferably after polymerisation, for example by mixing at least one of the compounds of the formula I, and further additives if desired, into the melt in accordance with the methods customary in the art, before or during shaping, or by applying the dissolved or dispersed compounds to the polymer, where appropriate with subsequent evaporation of the solvent.

In the case of crosslinked polyethylene, the compounds are added before the crosslinking.

The following new compounds are, for example, particularly suitable for use as metal deactivators:

[Structure: bis(salicyloylhydrazino)-s-triazine with substituent X]

X = —O—CH₂—CH₂—CH₃

—N(morpholino)O

—NH—C₈H₁₇(u)

—CH₂—CH₂—CH₃

—⟨phenyl⟩

—NH—⟨phenyl⟩

The following new compounds are for example particularly suitable for use as antioxidants: 2-(octadecylamino)-4,6-disalicyloylhydrazino-s-triazine, 2-(di-2-ethylhexylamino)-4,6-bis-(2-hydroxy-5-tert.-butylbenzoylhydrazino)-s-triazine, 2-(dioctadecylamino-4,6-bis-(2-hydroxy-5-tert.-octylbenzoylhydrazino)-s-triazine, 2-dioctadecylamino-4,6-bis-(2-hydroxy-4-octoxybenzoylhydrazino)-s-triazine, 2-(di-2-ethylhexyl-amino)-4,6-bis-(2-hydroxy-4-butoxybenzoylhydrazino)-s-triazine, 2-(di-isopropylamino)-4,6-bis-(2-hydroxy-4-octoxy-benzoylhydrazino)-s-triazine, 2-propoxy-4,6-bis-(2-hydroxy-4-octoxybenzoylhydrazino)-s-triazine, and compounds of the formula

[Structure: bis(3,5-di-tert-butyl-salicyloylhydrazino)-s-triazine with substituent X]

in which X denotes the radicals

—O—CH₂—CH₂—CH₃

—N(morpholino)O

—NH—C₈H₁₇

—CH₂—CH₂—CH₃

—⟨phenyl⟩

—NH—⟨phenyl⟩

As further additives, together with which the stabilisers usable according to the invention can be employed, there may be mentioned:

1. Antioxidants of the aminoaryl and hydroxyaryl series. Amongst the latter, the sterically hindered phenol compounds should be mentioned, for example: 2,2'-thiobis-(4-methyl-6-tert.-butylphenol), 4,4'-thio-bis-(3-methyl-6-tert.-butylphenol), 2,2'-methylene-bis-(4-methyl-6tert.-butylphenol), 2,2'-methylene-bis-(4-ethyl-6-tert.-butylphenol), 4,4'-methylene-bis-(2-methyl-6-tert.-butylphenol), 4,4'-butylidene-bis-(3-methyl-6-tert.-butylphenol), 2,2'-methylene-bis-[4-methyl-6-(α-methylcyclohexyl)-phenol], 2,6-di-(2-hydroxy-3-tert.-butyl-5-methylbenzyl)-4methylphenol, 2,6-di-tert.-butyl-4-methylphenol, 1,1,3-tris-2-methyl-(4-hydroxy-5-tert.-butyl-phenyl)-butane, 1,3,5-trimethyl-2,4,6-tri-(3,5-di-tert.-butyl-4-hydroxybenzyl)-benzene, esters of β-4-hydroxy-3,5-di-tert.-butyl-phenyl-propionic acid with monohydric or polyhydric alcohols, such as methanol, ethanol, octadecanol, hexanediol, nonanediol, trimethylhexanediol, thiodiethylene glycol, trimethylolethane or pentaerythritol, 2,4-bis-octylmercapto-6-(4-hydroxy-3,5-di-tert.-butylanilino)-s-triazine, 2,4-bis-(4-hydroxy-3,5-di-tert.-butylphenoxy)-6-octylmercapto-s-triazine, 1,1-bis-(4-hydroxy-2-methyl-5-tert.-butyl-phenyl)-3-dodecylmercapto-butane, 4-hydroxy-3,5-di-tert.-butylbenzyl-phosphonic acid esters, such as the dimethyl, diethyl or dioctadecyl ester, (3-methyl-4-hydroxy-5-tert.-butylbenzyl)-malonic acid dioctadecyl ester, s-(3,5-dimethyl-4-hydroxyphenyl-thioglycollic acid octadecyl ester, and esters of bis-(3,5-di-tert.-butyl-4-hydroxybenzyl)-malonic acid, such as the didodecyl ester, dioctadecyl ester and 2-dodecylmercapto-ethyl ester.

Amongst the aminoaryl compounds, there should be mentioned aniline and naphthylamine derivatives, and their heterocyclic derivatives, for example, phenyl-1-naphthylamine, phenyl-2-naphthylamine, N,N'-diphenyl-p-phenylenediamine, N,N'-di-2-naphthyl-p-phenylenediamine, N,N'-di-sec.-butyl-p-phenylenediamine, 6-ethoxy-2,2,4-trimethyl-1,2-dihydroquinoline, 6-dodecyl-2,2,4-trimethyl-1,2-dihydroquinoline, mono- and di-octyliminodibenzyl, and polymerised 2,2,4-trimethyl-1,2-dihydroquinoline, though on combined use of the compounds of the formula I with the abovementioned amine compounds the stabilised polymer no longer possesses such good colour properties, because of the tendency to discolouration of the abovementioned amine compounds.

2. UV-absorbers and light protection agents, such as:

a. 2-(2'-hydroxyphenyl)-benztriazoles, for example the 5'-methyl, 3',5'-di-tert.-butyl, 5'-tert.-butyl, 5-chloro-3',5'-di-tert.-butyl, 5-chloro-3'-tert.-butyl, 5'-methyl, 3',5'-di-tert.-amyl, 3'-methyl-5'-β-carbomethoxyethyl and 5-chloro-3',5'-di-tert.-amyl derivative, b. 2,4-bis-(2'-hydroxyphenyl)-6-alkyl-s-triazines, for example the 6-ethyl or 6-undecyl derivative, c. 2-hydroxy-benzophenones, for example the 4-hydroxy, 4-methoxy, 4-octoxy, 4-decyloxy, 4-dodecyloxy, 4,2',4'-trihydroxy or 2'-hydroxy-4,4'-dimethoxy derivative, d. 1,3-bis-(2'-hydroxy-benzoyl)-benzenes, for example 1,3-bis-(2'-hydroxy-4'-hexyloxy-benzoyl)-benzene, 1,3-bis-(2'-hydroxy-4'octoxy-benzoyl)-benzene and 1,3-bis-(2'-hydroxy-4'-dodecyloxy-benzoyl)-benzene.

e. Aryl esters of optionally substituted benzoic acids, such as phenyl salicylate, octylphenyl salicylate, benzoyl-resorcinol, dibenzoyl-resorcinol, 3,5-di-tert.-butyl-4-hydroxybenzoic acid 2,4-di-tert.-butyl-phenyl ester or octadeyl ester.

f. Acrylates, for example α-cyano-β,β-diphenylacrylic acid ethyl ester or isooctyl ester, α-carbomethoxycinnamic acid methyl ester, α-cyano-β-methyl-p-methoxy-cinnamic acid methyl ester or butyl ester, and N-(β-carbomethoxy-vinyl)-2-methylindoline.

g. Nickel compounds, for example nickel complexes of 2,2'-thiobis-(4-tert.-octylphenol), such as the 1:1 and 1:2 complex, optionally with other ligands such as n-butylamine, nickel complexes of bis-(4-tert.-octylphenyl)-sulphone, such as the 2:1 complex, optionally with other ligands such as 2-ethylcaproic acid, nickel dibutyldithiocarbamate, nickel salts of 4-hydroxy-3,5-di-tert.-butylbenzyl-phosphonic acid monoalkyl esters, such as the methyl, ethyl or butyl ester, and the nickel complex of 2-hydroxy-4-methyl-phenyl-undecylketone-oxime.

h. Oxalic acid diamides, for example 4,4'-dioctyloxy-oxanilide, 2,2'-di-octyloxy-5,5'-di-tert.-butyloxanilide and 2,2'-di-dodecyloxy-5,5'-di-tert.-butyloxanilide.

3. Phosphites, such as triphenylphosphite, diphenylalkylphosphites, phenyldialkylphosphites, trinonylphenylphosphite, trilaurylphosphite, trioctadecylphosphite, 3,9-di-isodecyloxy-2,4,8,10-tetraoxa-3,9-diphosphaspiro-(5,5)-undecane and tri-(4hydroxy-3,5-di-tert.-butylphenyl)-phosphite.

4. Nucleating agents, such as 4-tert.-butylbenzoic acid, adipic acid and diphenylacetic acid.

5. Compounds which destroy peroxide, such as esters of β-thiodipropionic acid, for example the lauryl, stearyl, myrystyl or tridecyl ester. Salts of 2-mercaptobenzimidazole, for example the zinc salt, or diphenylthiourea.

6. Other additives, such as plasticisers, anti-static agents, flameproofing agents, blowing agents, pigments, carbon black, asbestos, glass fibres, kaolin and talc.

When using the stabilisers according to the invention in combination with phenolic antioxidants, particularly good stabilising effects are achieved if compounds which destroy peroxides, such as higher alkyl esters of thiodipropionic acid, are used simultaneously, since these compounds which destroy peroxide do not only, as is known, show synergism with the phenolic antioxidants, but also with the stabilisers of the formula I.

The polyolefines stabilised by addition of the compounds according to the invention are particularly suitable for use as coating material for copper wires and cables, but also for use for other types of metal coating and for the manufacture of shaped articles, such as films, filaments, foils, pipes, injection-moulded articles and the like. They can even be used mixed with copper or pigments containing copper. The invention is explained in more detail in the Examples which follow.

EXAMPLE 1

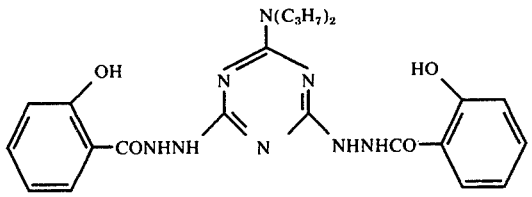

a. 25 g of hydrazine hydrate in 25 ml of dioxane are first introduced into the reaction vessel, and are slowly treated with a solution of 24.9 g of 2-(di-n-propylamino)-4,6-dichloro-s-triazine in 80 ml of dioxane at approx. 30° C, whilst stirring and cooling externally. The reaction mixture is heated to the boil under reflux for 3 hours. On cooling, 2-(di-n-propylamino)-4,6-dihydrazino-s-triazine precipitates as a white, micro-crystalline powder. It is filtered off, freed of adhering hydrazine hydrochloride by intensive washing with cold water, and, if desired, further purified by recrystallisation from dioxane. The compound melts at 105° C.

The reaction can also be carried out by only employing 2 mols of hydrazine hydrate per mol of dichlorotriazine, and binding the hydrogen chloride formed in the reaction by simultaneous addition of 1.8 mols of concentrated sodium hydroxide solution.

b. 24 g. of 2-(di-n-propylamino)-4,6-dihydrazino-s-triazine are dissolved in approx. 300 ml of dimethylacetamide and are treated with 32 g of salicyloyl chloride at room temperature over the course of 30 minutes. The reaction is exothermic and cooling is therefore necessary. The homogeneous reaction mixture is stirred for a further 30 minutes at room temperature and is then slowly poured into 500 to 1000 ml of ice water whilst stirring, whereupon the reaction product precipitates as a white solid. The product is dissolved in dimethylacetamide, carefully precipitated with water, filtered off, washed with ethanol and subsequently dried at 70° C. 2-(Di-n-propylamino)-4,6-di-salicyloyl-hydrazino-s-triazine (Stabiliser No. 1) is thus obtained in the form of a white, crystalline powder of melting point 254°–5° C.

If, in this Example, the salicyloyl chloride is replaced by the equimolar amount of one of the acid chlorides of Table 1 below, and an analogous procedure is followed, the corresponding substituted 2-(di-n-propylamino)-4,6-disalicyloylhydrazino-s-triazines, having the melting points indicated, are obtained:

Table 1

| Acid chloride | Melting point of the diacylhydrazinotriazine |
|---|---|
| ![CH₃-C₆H₃(OH)-COCl] | 258–260° C (from dimethylformamide/water) (Stabliser No. 2) |
| ![Cl-C₆H₃(OH)-COCl] | 275–276° C (from dimethylformamide/water) (Stabiliser No. 3) | of, washed with water, dried at 80° C and purified by recrystallisation from dioxane. The 2-propoxy-4,6-disalicyloylhydrazino-s-triazine obtained (Stabiliser No. 4) has a melting point of 258°–260° C.

If, in this Example, 2-(propoxy)-4,6-dihydrazino-s-triazine is replaced by the equimolar amount of one of the dihydrazinotriazines of Table 2 below, and an analogous procedure is followed, the disalicyloylhydrazino-s-triazines which are correspondingly substituted in the 2-position, having the melting points indicated, are obtained:

Table 2

| Dihydrazino-s-triazine | Melting point of the reaction product |
|---|---|
| NH₂NH—C(=N)—N=C(R)—N=C—NHNH₂ | HO-C₆H₄-CONHNH—C(=N)—N=C(R)—N=C—NHNHCO-C₆H₄-OH |
| R = N(CH₃)₂ melting point: 186° C | Stabiliser No. 5 296–8° C (from dimethylformamide/water) |
| R = N(morpholino) O melting point: 220° C | Stabiliser No. 6 260° C (from acetonitrile) |
| R = NHCH₃ melting point: 260° C | Stabiliser No. 7 >150° C (from acetone/water) |
| R = NHC₃H₇ melting point: 198° C | Stabiliser No. 8 195° C (from acetonitrile) |
| R = NHC₈H₁₇ melting point 165° C | Stabiliser No. 9 210–212° C (from acetonitrile) |
| R = C₃H₇ melting point: 158° C | Stabiliser No. 10 268° C (from isopropanol) |

EXAMPLE 2

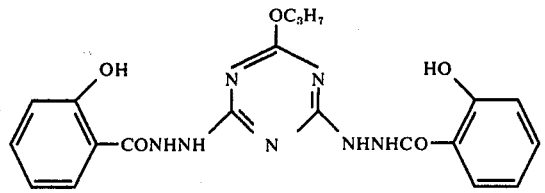

20 g of 2-propoxy-4,6-dihydrazino-s-triazine (melting point 130° C) are dissolved in 200 ml of dimethylacetamide and treated with 32 g of salicyloyl chloride at 10° – 20°, over the course of 30 minutes, whilst stirring and cooling externally. The reaction is exothermic. The homogeneous reaction mixture is stirred for a further 30 minutes at 20° C and is subsequently clarified by filtration and slowly treated with 500 ml of water whilst stirring, whereupon the reaction product precipitates as a white solid. The precipitate is filtered

EXAMPLE 3

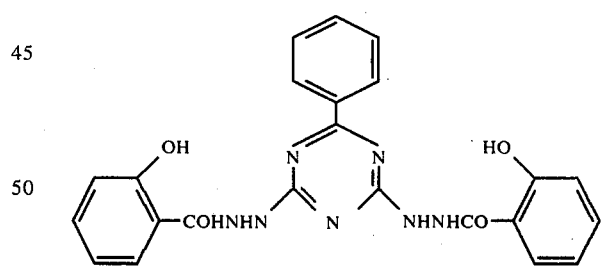

21.7 g of 2-phenyl-4,6-dihydrazino-s-triazine (melting point: 228° C) are suspended in 200 ml of dimethylacetamide and 32 g of salicyloyl chloride are added over the course of 30 minutes at room temperature, whilst stirring and cooling externally. The reaction is exothermic. The homogeneous reaction mixture is stirred for a further 30 minutes at room temperature and is then clarified by filtration and slowly poured into 700 ml of water, whilst stirring, whereupon the reaction product precipitates as a yellowish-white solid. The precipitate is filtered off, washed with water, dried at 80° C and purified by precipitation with water from dimethylacetamide solution, and after drying is optionally still digested with hot acetonitrile. The resulting 2-phenyl-4,6-disalicyloylhydrazino-s-triazine (Stabiliser No. 11) has a melting point of 267°–268° C.

If, in this Example, 2-phenyl-4,6-dihydrazino-s-triazine is replaced by the equivalent quantity of one of the dihydrazinotriazines of Table 3 below, and the analogous procedure is followed, the correspondingly 2-substituted disalicyloylhydrazino-s-triazines are obtained, initially in the form of almost white, high-melting crude products, which can be purified by recrystallisation from dimethylformamide/H₂O or from acetonitrile:

Table 3

| R | Melting point |
|---|---|
| —H | 218° C |
| —CH₃ | 111° C |
| —N(C₂H₅)₂ | 114° C |
| —N(n-C₄H₉)₂ | 127° C |
| —N(C₆H₅)₂ | 240° C |
| —N(CH₃)—C₆H₅ | 171° C |
| —O-n-C₄H₉ | 108° C |

EXAMPLE 4

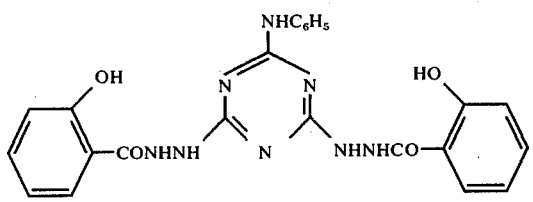

a. 23.2 g of 2-anilino-4,6-dihydrazino-s-triazine (melting point: 239°) are suspended in 300 ml of dimethylacetamide and treated with 32 g of salicyloyl chloride over the course of 30 minutes, at approx. 20° C, whilst stirring and cooling externally. The reaction is exothermic. The homogeneous reaction mixture is stirred for a further 30 minutes at 20° C and is subsequently clarified by filtration and slowly poured into about 700 ml of water at 80° C, whilst stirring. Hereupon, the reaction product precipitates as a white solid. After cooling, it is filtered off, washed with water and dried at approx. 70° C. The 2-anilino-4,6-disalicyloylhydrazino-s-triazine thus obtained (Stabiliser No. 12) melts at approx. 170°, with slow decomposition. If desired, the compound can be further purified by precipitation with water from dimethylacetamide solution.

b. The same compound is obtained in a somewhat less pure form in the following manner:

18.4 g of cyanuric chloride are dissolved in 200 ml of methyl ethyl ketone and 30.4 g of salicylic acid hydrazide and 10.6 g of anhydrous sodium carbonate are simultaneously added, in portions, at 5° C, whilst stirring and cooling. The reaction mixture is stirred for a further 2 hours at 10° C and then 9.3 g of aniline and 10 ml of 10 N sodium hydroxide solution are added simultaneously at about 20° C. Thereafter the mixture is heated to the boil under reflux for 5 hours, with continued stirring. After cooling, the precipitate is filtered off and washed with water until it is free of salt. If desired, the 2-anilino-4,6-salicyloylhydrazino-s-triazine thus obtained can be further purified by dissolving it in dimethylacetamide and precipitating with water. The substance melts above 170° C, with slow decomposition.

EXAMPLE 5

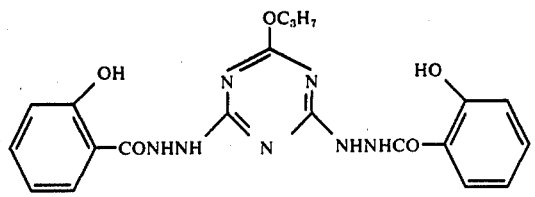

20.8 g of 2-propoxy-4,6-dichloro-s-triazine are dissolved in 200 ml of dimethylacetamide at 20° C. 15.2 g of salicylic acid hydrazide are added to this solution, whilst stirring, followed by 10 ml of 10 N sodium hydroxide solution added slowly. The reaction is exothermic and the temperature is kept at 20° C by external cooling. After 30 minutes, a further 15.2 g of salicylic acid hydrazide and a further 10 ml of 10 N sodium hydroxide solution are added. The reaction mixture is then further heated to the boil under reflux for 3 hours. The sodium chloride formed hereupon precipitates. After cooling, the reaction solution is freed of sodium chloride and undissolved impurities by filtration and is poured into 500 ml of water. Hereupon, the reaction product precipitates as a white solid. After filtering off, the 2-propoxy-4,6-disalicyloylhydrazino-s-triazine obtained (Stabiliser No. 4) is washed with water, and the moist filter cake is thoroughly digested with ethanol and finally dried in vacuo at 100°. The compound forms white crystals of melting point 256° C.

By way of example, 2-(di-n-propylamino)-4,6-disalicyloylhydrazino-s-triazine (melting point 254° C, Stabiliser No. 1) and 2-n-propylamino-4,6-disalicyloylhydrazino-s-trianine of melting point 195° C (Stabiliser No. 8) are also obtained in the same manner if, in the present example, 2-propoxy-4,6-dichloro-s-triazine is replaced by an equivalent amount of 2-(di-n-propylamino)-4,6-dichloro-s-triazine or 2-n-propylamino-4,6-dichloro-s-triazine respectively.

EXAMPLE 6

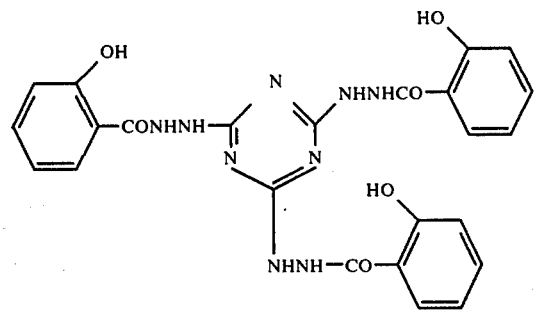

clarifying a. 34.2 g of 2,4,6-trihydrazino-s-triazine are suspended in 500 ml of dimethylacetamide and 93.6 g of salicyloyl chloride are slowly added at 10°–15° C, whilst stirring. After stirring for 1½ hours at about 20° C, the reaction mixture forms a fairly homogeneous solution, which is clarified by filtration and allowed to run into 1 litre of cold water. The yellowish precipitate is thoroughly washed with water and the moist filter cake is purified by dissolving it in acetone, clarifying the solution by filtration and precipitating the product with water. A further purification is achieved by re-precipitating from dioxane solution with water.

The 2,4,6-trisalicyloylhydrazino-s-triazine obtained (Stabiliser No. 13) is dried in vacuo at about 60° C. The compound decomposes above 180° C.

b. The same compound is also obtainable in the following manner:

18.4 g of cyanuric chloride are dissolved in 200 ml of methyl ethyl ketone and 45.6 g of salicylic acid hydrazide and 30 ml of 10 N sodium hydroxide solution are simultaneously added in portions, at 5° C, whilst stirring and cooling. Thereafter the reaction mixture is stirred for a further 3 hours at 50° C and is then allowed to cool to room temperature and run into 500 ml of water. The yellowish-white solid which hereupon precipitates is filtered off and washed with water. The further purification of the 2,4,6-trisalicyloylhydrazino-s-triazine thus obtained can be carried out as described above.

EXAMPLE 7 desired, further purified by recrystallisation from dioxane.

b. 38 g of 2-(di[2-ethylhexyl]-amino)-4,6-dihydrazino-s-triazine are dissolved in 350 ml of dimethylacetamide and 32 g of salicyloyl chloride are added over the course of 30 minutes at room temperature. The reaction is exothermic. The homogeneous reaction mixture is stirred for a further 30 minutes at room temperature and is then poured into 1000 ml of ice water whilst stirring, whereupon the reaction product precipitates as a white solid. The product is dissolved in dimethylacetamide, carefully precipitated with water, filtered off, washed with ethanol and subsequently dried at 70° C. 2-(Di-[2-ethylhexyl]-amino)-4,6-disalicyloylhydrazine-s-triazine (Stabiliser No. 14) is thus obtained in the form of a white, crystalline powder of melting point 176° – 177°.

If, in this Example, 2-(di-[2-ethylhexyl]-amino)-4,6-dihydrazino-s-triazine is replaced by the equimolar amount of one of the dihydrazinotriazines of Table 3 below, and an analogous procedure is followed, the disalicyloylhydrazino-s-triazines which are correspondingly substituted in the 2-position, having the melting points indicated, are obtained:

Table 3

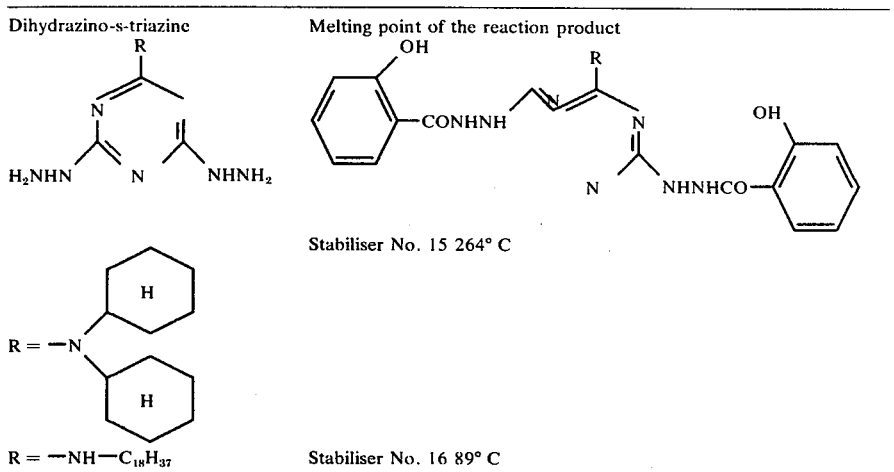

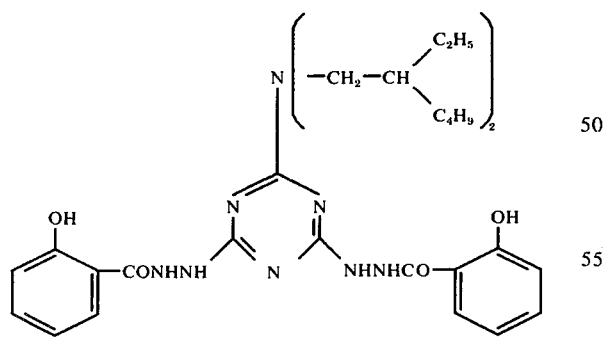

EXAMPLE 8

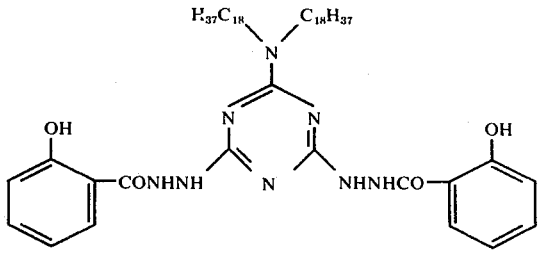

a. 25 g of hydrazine hydrate in 25 ml of dioxane are first introduced into the reaction vessel and are slowly treated with a solution of 38.9 g of 2-(di-[2-ethylhexyl]-amino)-4,6-dichloro-s-triazine in 120 ml of dioxane at approx. 30° C, whilst stirring and cooling externally. The reaction mixture is heated to the boil under reflux for 3 hours. On cooling, 2-(di-[2-ethylhexyl]-amino-4,6-dihydrazino-s-triazine precipitates as a white powder. It is filtered off, washed with cold water and, if a. 18.5 g of cyanuric chloride in 50 ml of chloroform are initially introduced into the reaction vessel and cooled to −5° C. A solution of 52 g of dioctadecylamine in 200 ml of chloroform is slowly added dropwise, whilst stirring and cooling externally, and subsequently the mixture is stirred for a further 5 minutes and then treated with a solution of 4.0 g of sodium hydroxide in 30 ml of water. The mixture is stirred for a further hour without external cooling, in the course of which the temperature slowly rises to room temperature.

The chloroform solution is separated from the aqueous phase, repeatedly washed with water, filtered, dried and evaporated. The crystalline residue is 2-(di-octadecylamino)-4,6-dichloro-s-triazine, which melts at 60° C.

b. 12.2 g of salicylic acid hydrazide are dissolved in 120 ml of dimethylacetamide at 60° C and treated with a solution of 26.8 g of 2-(di-octadecylamino)-4,6-dichloro-s-triazine in 120 ml of dimethylacetamide. The mixture is warmed to 120° C and kept for 3 hours at this temperature, 1.0 g of sodium hydroxide in 6 ml of water is then added dropwise, and the whole is stirred for a further 3 hours at 120° C and cooled. The solution is poured into 1500 ml of water whilst stirring, whereupon the product precipitates as a white solid. After filtration, it is dried and recrystallised from ethylene glycolmonomethyl ether. 2-(Di-octadecylamino)-4,6-disalicyloylhydrazino-s-triazine (Stabiliser No. 17) is thus obtained in the form of a white, crystalline powder of melting point 200° – 201° C.

If, in this Example, the salicylic acid hydrazide is replaced by the equimolar amount of one of the substituted salicylic acid hydrazides of Table 4 below, and an analogous procedure is followed, the corresponding substituted 2-(di-octadecylamino)-4,6-disalicyloyl-hydazino-s-triazines having the melting points indicated, are obtained:

Table 4

| Salicylic acid hydrazide | Melting point of the di-salicyloyl-hydrazino-triazine |
|---|---|
| CONHNH₂, OH, OC₈H₁₇ | Stabilier No. 18 189 – 191 ° C |

Table 4-continued

| Salicylic acid hydrazide | Melting point of the di-salicyloyl-hydrazino-triazine |
|---|---|
| CONHNH₂, OH, 1,1,3,3-tetramethylbutyl | Stabiliser No. 19 228 – 230° C |
| CONHNH₂, OH, tert. butyl | Stabiliser No. 20 221 – 223' C |

EXAMPLE 9

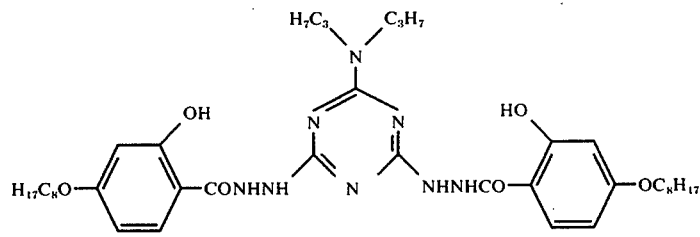

22.6 g of 2-hydroxy-4-octoxy-benzhydrazide are dissolved in 200 ml of dimethylacetamide at 60° C and treated with a solution of 10 g of 2-(di-n-propylamino)-4,6-dichloro-s-triazine in 50 ml of dimethylacetamide whilst keeping the temperature constant. The reaction mixture is heated to 120° C over the course of 3 hours. After cooling, it is poured into one litre of water, whereupon the product precipitates as a white solid. After filtration, it is dried and recrystallised from ethylene glycol-monomethyl ether. 2-(Di-n-propylamino)-4,6-di-(2-hydroxy-4-octoxybenzoylhydrazino)-s-triazine (Stabiliser No. 21) is thus obtained in the form of a white powder of melting point 195° – 196° C.

EXAMPLE 10

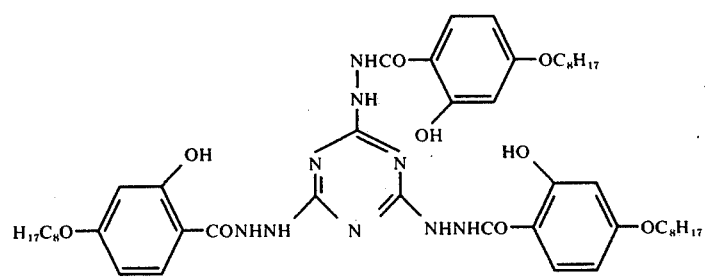

36.8 g of 2-hydroxy-4-octoxy-benzhydrazide are dissolved in 200 ml of dimethylacetamide at room temperature, and a solution of 8.0 g of cyanuric chloride in 100 ml of dimethylacetamide is slowly added. The reaction mixture is warmed to 60° C, 10.4 g of pyridine in 50 ml of dimethylacetamide are added dropwise at this temperature, and the temperature is then further raised as far as 90° C. After stirring for 2 hours, the mixture is cooled and poured into one litre of water, whereupon the product precipitates. After filtration, it is dried and recrystallised from ethylene glycol-monomethyl ether. 2,4,6-Tri-s-(2-hydroxy-4-octoxybenzoylhydrazino)-3-triazine (Stabiliser No. 22) is thus obtained in the form of a white powder of melting point 155° C. The preparation thus produced still contains about 0.5% of water.

The previously known stabilisers for polyolefines listed in Table 5 below were also tested as comparison compounds in the test examples which follow:

Table 5

| Stabiliser No. | Chemical description |
|---|---|
| 23 | N-salicyloyl-hydrazine |
| 24 | N-acetyl-N'-salicyloyl-hydrazine |
| 25 | N-salicyloyl-N'-salicylidene-hydrazine |

EXAMPLE 11 a. Manufacture of the test specimens.

100 parts of polypropylene (melt index 3.2 g/10 mins., 230° C/2160 g) are thoroughly mixed for 10 minutes, in a shaking apparatus, with 0.1 of β-(3,5-di-tert.butyl-4-hydroxyphenyl)-propionic acid octadecyl ester, 0.3 part of dilaurylthiodipropionate and 0.5 part of an additive listed in Table 6 below.

The resulting mixture is kneaded in a Brabender plastograph at 200° C for 10 minutes, 1.0% by weight of powdered copper (manufactured electrolytically, Merck) is then added, and the whole is thoroughly mixed at the same temperature for a further 2 minutes. The composition thus obtained is subsequently pressed in a platen press at 260° C platen temperature to give 1 mm thick sheets, from which strips of 1 cm width and 17 cm length are punched by means of a punch tool.

The fully stabilised test specimens without addition of copper, or with addition of copper but without metal deactivator, which are required for comparison purposes, are manufactured analogously.

b. Test.

The test for effectiveness of the metal deactivators added to the test strips containing copper is carried out by heat ageing in a circulating air oven at 149° or 135° C, and is compared with test strips which do not contain copper. For this purpose, 3 test strips of each formulation are employed. The incipient, easily visible decomposition of the test strip is defined as the end point.

Table 6

Oven ageing times

| Stabiliser No. | Test temperature, °C | Days until decomposition starts without addition of copper | with addition of copper |
|---|---|---|---|
| without additive | 149 | 20 | <<1 |
|  | 135 | 90 | <1 |
| 1 | 149 | 31 | 10 |
|  | 135 | 199 | 77 |
| 2 | 149 | 29 | 10 |
|  | 135 | 125 | 55 |
| 3 | 149 | 27 | 17 |
|  | 135 | 115 | 75 |
| 4 | 149 | 30 | 25 |
|  | 135 | 155 | 125 |
| 5 | 149 | 15 | 6 |
|  | 135 | 96 | 53 |
| 6 | 149 | 20 | 17 |
|  | 135 | 95 | 71 |
| 7 | 149 | 18 | 13 |
|  | 135 | 83 | 57 |
| 8 | 149 | 26 | 19 |
|  | 135 | 158 | 58 |
| 9 | 149 | 33 | 25 |
|  | 135 | 172 | 155 |
| 10 | 149 | 30 | 27 |
|  | 135 | 151 | 72 |
| 11 | 149 | 20 | 20 |
|  | 135 | 90 | 77 |
| 12 | 149 | 21 | 18 |
|  | 135 | 110 | 77 |
| 13 | 149 | 20 | 8 |
|  | 135 | 90 | 31 |

Comparison products

| Stabiliser No. | Test temperature, °C | Days until decomposition starts without addition of copper | with addition of copper |
|---|---|---|---|
| 23 | 149 | 27 | 8 |
|  | 135 | 90 | 24 |
| 24 | 149 | 20 | 4 |
|  | 135 | 90 | 27 |
| 25 | 149 | 19 | 16 |
|  | 135 | 86 | 2 |

EXAMPLE 12

The test specimens without addition of copper, described in Example 11, were furthermore tested for their colour stability, in particular:

a. After the incorporation process (Table 7, column 2)
b. After heat ageing at 149° C (Table 7, column 3)
c. After 1 week's treatment with boiling water (Table 7, column 4).

For Table 7, an empirical colour scale was used, in which 5 denotes absence of colour, 4 denotes a just perceptible slight discolouration and 3, 2, 1 and <1 denote progressively more intense discolouration.

Table 7

Test for colour stability (without addition of copper)

| Stabiliser No. | Colour assessment according to scale 1 to 5 | | |
|---|---|---|---|
|  | After incorporation | After heat ageing, 149° C | Boiling water, 1 week |
| without additive | 5 | 4 | 4 |
| 1 | 3 | 2 | 4 |
| 4 | 4 | 2 | 4 |
| 5 | 4 | 2 | 4 |
| 6 | 4 | 2 | 4 |
| 11 | 3 | 2 | 3 |
| 13 | 4 | 2 | 3 |
| Comparison products | | | |
| 23 | 1 | 1 | <1 |
| 24 | 1 | 2 | <1 |

Table 7-continued

Test for colour stability (without addition of copper)

| Stabiliser No. | Colour assessment according to scale 1 to 5 | | |
|---|---|---|---|
| | After incorporation | After heat ageing, 149° C | Boiling water, 1 week |
| 25 | 1 | <1 | 2 |

EXAMPLE 13

100 parts of polypropylene (melt index 3.2 g/10 mins., 230° C/2160 g) are thoroughly mixed for 10 minutes, as described in Example 11, in a shaking apparatus, with 0.5 part of the Stabiliser No. 5 and with the further additives listed in Table 8, in the concentrations indicated.

The resulting mixture is kneaded for 10 minutes in a Brabender plastograph at 200° C, 1.0% by weight of powdered copper (manufactured electrolytically, Merck) is then added, and the whole is thoroughly mixed at the same temperature for a further 2 minutes. The composition thus obtained is subsequently pressed in a platen press, at 260° C platen temperature, to give 1 mm thick sheets, from which strips of 1 cm width and 17 cm length are punched with the aid of a punch tool.

The fully stabilised test specimens without addition of copper, required for comparison purposes, are manufactured analogously.

The test of the dependence of the action of the Stabiliser No. 5 on the further additives is carried out by heat ageing in a circulating air oven at 149° C. The results are indicated in Table 8, column 3, and the oven ageing times of the test specimens without addition of copper, required for comparison, are indicated in column 2.

Table 8

Oven ageing times at 149° C

| Additives and concentration | Days until decomposition starts | |
|---|---|---|
| | without addition of copper | with addition of copper |
| 0.2 part of Additive A | 15 | 7 |
| 0.2 part of Additive B | 25 | 6 |
| 0.1 part of Additive C | 29 | 6 |
| 0.3 part of Additive D | 17 | 6 |
| 0.05 part of Additive E | | |
| 0.15 part of Additive D | 28 | 16 |
| 0.1 part of Additive B | | |
| 0.3 part of Additive D | 32 | 22 |
| 0.05 part of Additive E | 3 | 3 |

Similar favourable results are obtained if the polypropylene used additionally contains 20% of gas black.

EXAMPLE 14

100 parts of polypropylene (melt index 3.2 g/10 mins., 230° C/2160 g) are thoroughly mixed for 10 minutes, in a shaking apparatus, with the additives listed in Table 9, in the concentrations indicated.

The resulting mixture is kneaded for 10 minutes in a Brabender plastograph at 200° C, 0.1% by weight of copper stearate is then added, and the whole is thoroughly mixed at the same temperature for a further 2 minutes. The resulting composition is subsequently pressed in a platen press at 260° C platen temperature to give 1 mm thick sheets, from which strips of 1 cm width and 17 cm length are punched with the aid of a punch tool.

The stabilised test specimens without added copper stearate, required for comparison purposes, are manufactured analogously.

The test of the effectiveness of the metal deactivator (Stabiliser No. 5) in the test strips containing copper stearate is carried out by heat ageing in a circulating air oven at 149° C; for results, see Table 9, column 3. The oven ageing times of the test specimens without added copper stearate, which are required for comparison, are given in Table 9, column 2.

Table 9

Oven ageing times at 149° C

| Additives and concentration | Days until decomposition starts | |
|---|---|---|
| | without copper stearate | with copper stearate |
| 0.2 part of Additive A without metal deactivator | 15 | <<1 |
| 0.2 part of Additive A 0.5 part of Stabiliser No. 5 | 15 | 3 |
| 0.1 part of Additive B 0.3 part of Additive D 0.5 part of Stabiliser No. 5 | 32 | 16 |

The coding of the additives is the same as in Examples 7–9.

EXAMPLE 15

100 parts of polypropylene (melt index 3.2 g/10 mins., 230° C/2160 g) are thoroughly mixed, in a shaking apparatus, with 0.1 part of 3-(3,5-ditert.-butyl-4-hydroxyphenyl)-propionic acid octadecyl ester, 0.3 part of dilauryl-thiodipropionate and an additive listed in Table V below, in the amount indicated.

The resulting mixture is kneaded for 10 minutes in a Brabender plastograph at 200° C, 1.0% by weight of powdered copper (manufactured electrolytically, Merck) is then added, and the whole is thoroughly mixed for a further 2 minutes at the same temperature. The resulting composition is subsequently pressed in a platen press, at 260° C platen temperature, to give 1 mm thick sheets, from which strips of 1 cm width and 17 cm length are punched with the aid of a punch tool.

The test for effectiveness of the metal deactivators added to the test strips, as a function of the concentration, is effected by heat ageing in a circulating air oven at 149° and 135° C. The results are given in Table 10, columns 3 to 6.

Table 10

Oven ageing times

| Stabiliser No. | Test temperature, ° C | Days until decomposition starts | | | |
|---|---|---|---|---|---|
| | | 0.1 part | 0.2 part | 0.3 part | 0.5 part concentration |
| | 149 | 2 | 12 | 11 | 18 |

Table 10-continued

Oven ageing times

| Stabiliser No. | Test temperature, °C | Days until decomposition starts | | | |
|---|---|---|---|---|---|
| | | 0.1 part | 0.2 part | 0.3 part | 0.5 part concentration |
| 4 | 135 | 9 | 83 | 72 | 102 |
| | 149 | 3 | 5 | 6 | 6 |
| 5 | 135 | 24 | 51 | 72 | 71 |
| | 149 | 6 | 14 | 12 | 7 |
| 8 | 135 | 52 | 90 | 90 | 83 |
| | 149 | 9 | 14 | 15 | 17 |
| 9 | 135 | 70 | 100 | 100 | 102 |
| | 149 | 11 | 14 | 15 | 15 |
| 10 | 135 | 90 | 100 | 100 | 102 |

EXAMPLE 12

100 parts of polypropylene (melt index 3.2 g/10 mins., 230° C/2160 g) are thoroughly mixed for 10 minutes, in a shaking apparatus, with 0.2 part of an additive listed in Table 11 below.

The mixture obtained is kneaded for 10 minutes in a Brabender plastograph at 200° C, and the composition thus obtained is subsequently pressed in a platen press, at 260° C platen temperature, to give 1 mm thick sheets from which strips of 1 cm width and 17 cm length are punched.

The test for effectiveness of the additives added to the test strips, in their capacity of antioxidants, is effected by heat ageing in a circulating air oven at 135° C and 149° C, using an additive-free test strip for comparison. For this purpose, 3 test strips are employed of each formulation. The incipient, easily visible decomposition of the test strip is defined as the end point. The results are quoted in days.

Table 11

| Stabiliser No. | Days until decomposition starts | |
|---|---|---|
| | 149° C | 135° C |
| without additive | ½ | 1 |
| 14 | 13 | 83 |
| 9 | 6 | 55 |
| 15 | 4 | 49 |
| 16 | 11 | 56 |
| 17 | 4 | 52 |
| 18 | 12 | 52 |
| 19 | 12 | 65 |
| 20 | 12 | 67 |
| 21 | 5 | 68 |
| 22 | 5 | 58 |
| Comparison products | | |
| 23 | ½ | 1 |
| 24 | ½ | 1 |
| 25 | ½ | 1 |

EXAMPLE 13

The test specimens described in Example 12 were tested additionally for their colour stability, in particular:
a. After incorporation (Table 12, column 2)
b. After 500 hours' exposure to light in a Xenotest apparatus of Messrs. Hanau (Table 12, column 3)
c. After 1 week's treatment with boiling water (Table 12, column 4).

An empirical colour scale was used for Table 12, in which 5 denotes absence of colour, 4 denotes a just perceptible, slight discolouration, and 3, 2, 1 and <1 denote progressively more intense discolouration.

Table 12

Test for Colour Stability

| Stabiliser No. | Colour rating according to scale 1 - 5 | | |
|---|---|---|---|
| | After incorporation | After exposure to light | Boiling water, 1 week |
| 14 | 3 | 4 | 2 |
| 17 | 3 | 4 | 2 |
| 18 | 3 | 5 | 3 |
| 19 | 4 | 5 | 4 |
| 20 | 4 | 5 | 4 |
| Comparison products | | | |
| 23 | 1 | 2 | 1 |
| 24 | 2 | 2 | 1 |
| 25 | 1 | 1 | <1 |

EXAMPLE 14

100 parts of polypropylene (melt index 3.2 g/10 mins., 230° C/2160 g) are thoroughly mixed for 10 minutes, in a shaking apparatus, with 0.1 part of 3-(3,5-di-tert.-butyl-4-hydroxyphenyl)-propionic acid octadecyl ester (Additive A) and 0.3 part of dilauryl-thiodipropionate (Additive B) and 0.5 part of one of the additives listed in Table 13 below.

The resulting mixture is kneaded for 10 minutes in a Brabender plastograph at 200° C, and the composition thus obtained is subsequently pressed in a platen press, at 260° C platen temperature, to give 1 mm thick sheets, from which strips of 1 cm width and 17 cm length are punched.

The test for effectiveness of the additives added to the test strips, in their capacity as synergistically acting antioxidants in the presence of the Additives A and/or B, is effected by heat ageing in a circulating air oven at 135° C and 149° C, using, for comparison, a test strip which only contains the Additives A and B. For this purpose, three test strips of each formulation are used. The end point is defined as the incipient, easily visible decomposition of the test strips, and the results are quoted in days.

Table 13

| Stabiliser No. | Days until decomposition starts | |
|---|---|---|
| | 149° C | 135° C |
| without additive | 20 | 90 |
| 14 | 56 | 173 |
| 9 | 33 | 172 |
| 18 | 59 | 181 |
| 20 | 47 | 160 |
| 21 | 46 | 165 |
| Comparison products | | |
| 23 | 27 | 87 |
| 24 | 20 | 90 |
| 25 | 19 | 86 |

EXAMPLE 15

100 g of unstabilised high pressure polyethylene granules ("Plastylene" of Messrs. Ethylene Plastique, Mazingarbe, France) are thoroughly mixed, dry, with 1.0 g of 1,3-bis-(tert.-butyl-peroxyisopropylbenzene) (Perkadox 14 of Messrs. Oxydo GmbH, Emmerich, Germany) and 0.2 g of one of the additives of Table 14 below. The mixture is converted into a homogeneous mass over the course of 10 minutes on a friction roll mill at 110° C. This plastics mixture is pressed in a multi-daylight press at 260° C for 20 minutes to give 1 mm thick sheets, and under these conditions crosslinking of the polymer as a result of the peroxide added occurs. Test specimens of size 10 × 140 mm are punched from the sheets manufactured in this way by means of a punch tool.

The test specimens are suspended from V2A-steel stirrups and aged in a circulating air oven at 120° C and 150° C. After the expiration of an induction period which is characteristic of the additive, the degraded material drips away; the results are quoted in days.

Table 14

| Stabiliser No. | Days until material begins to drip away | |
|---|---|---|
| | at 120° C | at 150° C |
| without additive | 8 | 2 |
| 14 | 30 | 4 |
| 18 | 60 | 4 |
| 20 | 35 | 4 |
| 21 | 55 | 4 |
| Comparison products | | |
| 23 | 20 | 2 |
| 24 | 15 | 2 |
| 25 | 15 | 2 |

What we claim is:

1. Compounds of the formula

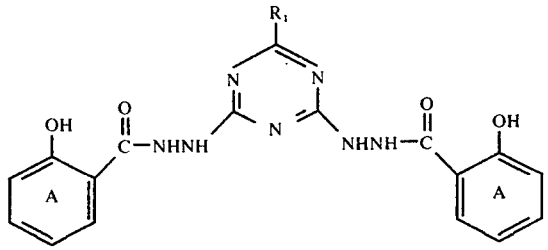

wherein $R_1$ is alkyl of 1 to 18 carbon atoms or alkoxy of 1 to 18 carbon atoms, groups or the group and the rings A are unsubstituted or are substituted by 1 to 2 alkyl groups with 1 to 8 carbon atoms each, an alkoxy group with 1 to 18 carbon atoms and/or 1 to 3 chlorine atoms.

2. Compounds according to claim 1, characterised in the $R_1$ denotes alkyl with 1 to 3 carbon atoms or alkoxy with 2 to 4 carbon atoms and $R_1$ and the substituents of A together contain at most 12 carbon atoms.

3. Compounds according to claim 1, characterised in that $R_1$ denotes alkyl with 1 to 4 carbon atoms or alkoxy with 1 to 8 carbon atoms, and the rings A are unsubstituted or are substituted by 1 to 2 alkyl groups with 1 to 12 carbon atoms each, an alkoxy group with 1 to 18 carbon atoms and/or chloride, with $R_1$ and the substituents of A together containing at least 13 carbon atoms.

4. The compound of claim 1 which is 2-propoxy-4,6-disalicyloylhydrazino-s-triazine.

5. The compound of claim 1 which is 2-propyl-4,6-disalicyloylhydrazino-s-triazine.

* * * * *